United States Patent [19]

Weadock et al.

[11] Patent Number: 5,716,660
[45] Date of Patent: Feb. 10, 1998

[54] TUBULAR POLYTETRAFLUOROETHYLENE IMPLANTABLE PROSTHESES

[75] Inventors: Kevin Weadock, Somerset; David J. Lentz, Randolph; Richard J. Zdrahala, Montville, all of N.J.

[73] Assignee: Meadox Medicals, Inc., Oakland, N.J.

[21] Appl. No.: 455,714

[22] Filed: May 31, 1995

Related U.S. Application Data

[62] Division of Ser. No. 289,790, Aug. 12, 1994.

[51] Int. Cl.$^6$ ........................................................ B05D 3/00
[52] U.S. Cl. .................... 427/2.25; 427/2.24; 427/338; 427/414
[58] Field of Search ................... 427/2.24, 2.25, 427/2.3, 2.31, 246, 338, 342, 389.9, 394, 414

[56] References Cited

U.S. PATENT DOCUMENTS

| | | |
|---|---|---|
| 3,106,483 | 10/1963 | Kline . |
| 3,272,204 | 9/1966 | Artandi et al. . |
| 3,276,448 | 10/1966 | Kronenthal . |
| 3,362,849 | 1/1968 | Tu .................................... 427/338 |
| 3,400,719 | 9/1968 | Buddecke ........................ 427/338 |
| 3,425,418 | 2/1969 | Chvapil et al. . |
| 3,479,670 | 11/1969 | Medell . |
| 3,483,016 | 12/1969 | McCool ............................ 427/338 |
| 3,688,317 | 9/1972 | Kurtz . |
| 3,808,113 | 4/1974 | Okamura et al. . |

(List continued on next page.)

FOREIGN PATENT DOCUMENTS

| | | |
|---|---|---|
| 000949A1 | 3/1979 | European Pat. Off. . |
| 0531547 | 3/1993 | European Pat. Off. . |
| 2209155 | 10/1970 | France . |
| 1491218 | 4/1969 | Germany . |
| 1494939 | 6/1969 | Germany . |
| 2129004 | 6/1971 | Germany . |
| 2601289 | 7/1977 | Germany . |
| 2843963 | 4/1980 | Germany . |
| 11 904693 | 2/1982 | U.S.S.R. . |
| 2 092 944 | 2/1982 | United Kingdom . |
| WO 82/03764 | 11/1982 | WIPO . |
| WO 83/03536 | 10/1983 | WIPO . |

OTHER PUBLICATIONS

R. Guidoin, et al., "Expanded Polytetrafluoroethylene Arterial Prostheses in Humans: Histopathological Study of 298 Surgically Excised Grafts," *Biomaterials*, 14, pp. 678–693 (1993). (No month available).

M. Kadletz, et al., "In Vitro Lining of Fibronectin Coated PTFE Grafts with Cryopreserved Saphenous Vein Endothelial Cells," *Thorac. Cardiovasc. Surgeon*, 35, pp. 143–147 (1987). (No month available).

J. Kaehler, et al., "Precoating Substrate and Surface Configuration to Determine Adherence and Spreading of Seeded Endothelial Cells on Polytetrafluoroethylene Grafts," *Journal of Vascular Surgery*, 9, pp. 535–541 (1989). (No month available).

P.B. Mansfield et al., "Preventing Thrombus on Artificial Vascular Surfaces: True Endothelial Cell Linings," *Trans. Amer. Artif. Int. Organs*, 21, pp. 264–272 (1975). (No month available).

L.R. Sauvage, et al., "Dacron® Arterial Grafts: Comparative Structures and Basis for Successful Use of Current Prostheses," *Vascular Graft Update: Safety and Performance, ASTM STP898*, pp. 16–24 (1986). (No month).

L.R. Sauvage, "Graft Complications in Relation to Prosthesis Healing," *Aortic and Peripheral Arterial Surgery*, pp. 427–440. (No month).

L.R. Sauvage, et. al., *Grafts for the 80's*, pp. 1–44 (1980). (No month).

*Primary Examiner*—Diana Dudash
*Attorney, Agent, or Firm*—Hoffmann & Baron, LLP

[57] ABSTRACT

An implantable prosthesis comprising an expanded polytetraethylene member having pores present in its wall structure wherein said pores contain a solid insoluble biocompatible, biodegradable material of natural origin. A process of preparing said prostheses is also disclosed.

8 Claims, 2 Drawing Sheets

U.S. PATENT DOCUMENTS

| | | | |
|---|---|---|---|
| 3,928,653 | 12/1975 | Dowell, Jr. et al. | |
| 3,953,566 | 4/1976 | Gore | 264/288 |
| 4,047,252 | 9/1977 | Liebig et al. | 3/1.4 |
| 4,113,912 | 9/1978 | Okita | 428/290 |
| 4,164,524 | 8/1979 | Ward et al. | 264/39 |
| 4,167,045 | 9/1979 | Sawyer | 3/1.4 |
| 4,193,138 | 3/1980 | Okita | 3/1.4 |
| 4,219,520 | 8/1980 | Kline | 264/629 |
| 4,229,838 | 10/1980 | Mano | 3/1.4 |
| 4,233,360 | 11/1980 | Luck et al. | 427/244 |
| 4,254,180 | 3/1981 | Kline | 428/323 |
| 4,332,035 | 6/1982 | Mano | 3/1.4 |
| 4,349,467 | 9/1982 | Williams et al. | |
| 4,355,426 | 10/1982 | MacGregor | 3/1.4 |
| 4,416,028 | 11/1983 | Eriksson et al. | 3/1.4 |
| 4,678,468 | 7/1987 | Hiroyoshi | 623/1 |
| 4,683,142 | 7/1987 | Zimmermann et al. | 427/414 |
| 4,713,070 | 12/1987 | Mano | 623/1 |
| 4,747,848 | 5/1988 | Maini | 623/1 |
| 4,776,853 | 10/1988 | Klement et al. | 8/94.11 |
| 4,784,659 | 11/1988 | Fleckenstein et al. | 623/1 |
| 4,804,381 | 2/1989 | Turina et al. | 623/1 |
| 4,814,120 | 3/1989 | Huc et al. | 264/28 |
| 4,822,361 | 4/1989 | Okita et al. | 623/12 |
| 4,841,962 | 6/1989 | Berg et al. | 128/156 |
| 4,842,575 | 6/1989 | Hoffman et al. | 600/36 |
| 4,871,361 | 10/1989 | Kira | 427/2.25 |
| 4,902,290 | 2/1990 | Fleckenstein et al. | 623/1 |
| 4,911,713 | 3/1990 | Sauvage et al. | 623/1 |
| 4,921,495 | 5/1990 | Kira | 623/1 |
| 4,973,609 | 11/1990 | Browne | 521/81 |
| 5,024,671 | 6/1991 | Tu et al. | 623/1 |
| 5,028,597 | 7/1991 | Kodama et al. | 514/56 |
| 5,034,265 | 7/1991 | Hoffman et al. | 428/253 |
| 5,037,377 | 8/1991 | Alonso | 600/36 |
| 5,061,276 | 10/1991 | Tu et al. | 623/1 |
| 5,061,281 | 10/1991 | Mares et al. | 623/11 |
| 5,098,779 | 3/1992 | Kranzler et al. | 428/306.6 |
| 5,108,424 | 4/1992 | Hoffman, Jr. et al. | 623/1 |
| 5,110,527 | 5/1992 | Harada et al. | 264/127 |
| 5,118,524 | 6/1992 | Thompson et al. | 427/2 |
| 5,120,833 | 6/1992 | Kaplan | 530/356 |
| 5,131,907 | 7/1992 | Williams et al. | 600/36 |
| 5,141,522 | 8/1992 | Landi | 623/66 |
| 5,178,630 | 1/1993 | Schmitt | 623/1 |
| 5,192,310 | 3/1993 | Herweck et al. | 623/1 |
| 5,197,977 | 3/1993 | Hoffman, Jr. et al. | |
| 5,221,698 | 6/1993 | Amidon et al. | 427/341 |
| 5,246,452 | 9/1993 | Sinnott | 623/1 |
| 5,275,838 | 1/1994 | Merrill | 427/2.24 |
| 5,318,524 | 6/1994 | Morse et al. | 606/214 |
| 5,324,647 | 6/1994 | Rubens | 427/2.25 |
| 5,494,744 | 2/1996 | Everhart et al. | 427/414 |
| 5,508,267 | 4/1996 | Czernuszka et al. | 427/414 |
| 5,536,656 | 7/1996 | Kemp et al. | 435/240.23 |
| 5,584,875 | 12/1996 | Duhamel et al. | 427/2.27 |
| 5,609,631 | 3/1997 | Rubens et al. | 427/2.31 |

TUBULAR POLYTETRAFLUOROETHYLENE IMPLANTABLE PROSTHESES

This is a divisional of copending application Ser. No. 08/289,790 filed on Aug. 12, 1994, pending.

FIELD OF THE INVENTION

The present invention relates to implantable devices made from expanded polytetrafluoroethylene (e-PTFE) having improved ability to bind with body tissues, higher resistance to suture leakage and enhanced blood tightness. More specifically, the present invention relates to a sheet or a tubular implantable prosthesis, e.g., vascular prostheses or surgical patches or mesh, having a porous e-PTFE structure, whereby said porous structure has a solid insoluble, biocompatible and biodegradable material of natural origin present in the pores.

BACKGROUND OF THE INVENTION e-PTFE porous tubes made by stretching and sintering have been used as tubular prostheses for artificial blood vessels for a number of years. These polymeric tubes have certain advantages over conventional textile prostheses, but also have disadvantages of their own. The e-PTFE tube has a microporous structure consisting of small nodes interconnected with many thin fibrils. The diameter of the fibrils, which depend on the processing conditions, can be controlled to a large degree and the resulting flexible structure has greater versatility in many aspects than conventional textile grafts. For example, e-PTFE grafts can be used in both large diameter, i.e. 6 mm or greater artificial blood vessels, as well as in diameters of 5 mm or less.

One particular problem, however, with expanded PTFE tubes, is their tendency to leak blood at suture holes and often propagate a tear line at the point of entry of the suture. As a result, numerous methods of orienting the node and fibril structure have been developed to prevent tear propagation. These processes are often complicated and require special machinery and/or materials to achieve this end.

Additionally, expanded PTFE arterial prostheses have been reported as suffering from poor, cellular infiltration and collagen deposition of the microporous structure by surrounding tissue. Numerous attempts to achieve improved blood compatibility and tissue binding properties have thus far fallen short. For example, in a study reported by Guidoin, et al., "Histopathology of Expanded PTFE", Biomaterials 1993, Volume 14, No. 9, cellular infiltration of the e-PTFE microporous structure was observed as being minimal. In an attempt to produce instant endothelial cell monolayers on graft surfaces, cryopreserved cultivated human saphenous vein endothelial cells were cultivated on reinforced PTFE prostheses. Prior to seeding of the endothelial cells on the prosthesis, the graft surface was precoated with human fibronectin. This study, reported by Kadletz, et al. in "Invitro Lining of Fibronectin Coated PTFE Grafts With Cryopreserved Saphenous Vein Endothelial Cells", Thorac. Cardiovasc. Surgeon 35 (1987) 143–147, reported discouraging results. More recently a study using laminin, collagen type I/III as well as fibronectin as precoating materials prior to seeding of endothelial cells on e-PTFE grafts was performed by Kaehler, et al., reported in "Precoating Substrate and Surface Configuration Determine Adherence and Spreading of Seeded Endothelial Cells on Polytetrafluoroethylene Grafts", Journal of Vascular Surgery, Volume 9, No. 4 April (1989). This study reported that cell adherence and cell spreading were distinctly superior on the surfaces which were precoated with fibronectin/type I/III collagen.

Thus far, e-PTFE substrates still suffer from endothelial cell adherence problems. The present invention is an attempt to address this problem, along with the problem of suture hole bleeding, by introducing into the porous walls of the e-PTFE prosthesis a solid natural material such as collagen, gelatin or derivatives of these materials. In addition to the above advantages, material such as collagen also serves to denucleate e-PTFE. Denuclearization removes air pockets and therefore reduces the thrombogenicity of the e-PTFE surface. Thus, the present invention seeks to improve prosthesis assimilation into the surrounding tissue, enhance the healing process as well as provide a more blood-tight prosthetic implant.

More recently, materials such as collagen and gelatin have been applied as coatings or as impregnations to textile grafts to avoid the need for preclotting the textile substrate prior to implantation. For example, U.S. Pat. Nos. 3,272,204, 4,842,575 and 5,197,977 disclose synthetic vascular grafts of this nature. Additionally, the '977 patent includes the use of active agents to enhance healing and graft acceptance once implanted in the body. The collagen source used in these patents is preferably from bovine skin or tendon dispersed in an aqueous solution that is applied to the synthetic textile graft by massaging or other pressure to cover the entire surface area and/or penetrate the porous structure.

U.S. Pat. No. 4,193,138 to Okita discloses a composite structure comprising a porous PTFE tube in which the pores of the tube are filled with a water-soluble polymer. The water-soluble polymer is used to form a hydrophilic layer which imparts an anti-thrombogenic characteristic to the e-PTFE tube. Examples of such polymers are polyvinylalcohol, polyethylene oxides, nitrogen-containing polymers and anionic polymers such as polyacrylic acid and polymethacrylic acid. Additionally, hydroxy esters or carboxy esters of cellulose and polysaccharides are also disclosed. This patent describes the diffusion of the water-soluble polymer into the pores of the tube and subsequent drying. The Water-soluble polymer is then subjected to a cross-linking treatment to render it insoluble in water. Cross-linking treatment such as heat treatment, acetalization, esterification or ionizing radiation-induced cross-linking reactions are disclosed. The water-soluble materials disclosed in this patent are synthetic in nature.

SUMMARY OF THE INVENTION

The prostheses of the present invention include expanded PTFE substrates having pores present in the substrate wall structure wherein said pores contain a solid biocompatible material of natural origin. These biocompatible, biodegradable materials are selected from generally extracellular matrix proteins as will be further described hereinbelow. Extracellular matrix proteins are known to be involved in cell-to-cell and cell-to-matrix adhesion mechanisms. The pores of the present invention are present in the expanded PTFE structure as the interstices of the node/fibril configuration. As previously mentioned, the pore size is dependent on the processing and stretching parameters used in preparation of the tubular substrate. For purposes of this invention, the term "pores" will be used interchangeably with other terms such as interstices, voids and channels.

The present invention also concerns a method of making the biomaterial-containing PTFE prostheses. The method involves contacting and/or filling the voids of the e-PTFE substrate with a fluid containing a soluble biocompatible material which is capable of solidifying and preferably cross-linking to form an insoluble material, and preferably cross-linking of the biocompatible material is accomplished once it has sufficiently contacted and/or filled the voids.

Once the biocompatible material is solidified and/or cross-linked in the voids of the e-PTFE substrate, it serves as a solid natural binding surface which tends to promote further endothelial cell attachment and tissue ingrowth which is so critical to proper prosthesis acceptance and healing. As previously noted, prior to the present invention, no existing method has resulted in good endothelial cell attachment, due to the inert chemical nature of the PTFE surface which allows the layers of endothelial cells to easily peel off. The present invention is an attempt to overcome such deficiencies. As importantly, the structure of the present invention assists in the denuclearization of the e-PTFE structure. Also, a reduction in suture hole bleeding is obtained.

DETAILED DESCRIPTION OF THE PREFERRED EMBODIMENT

Figure 1:
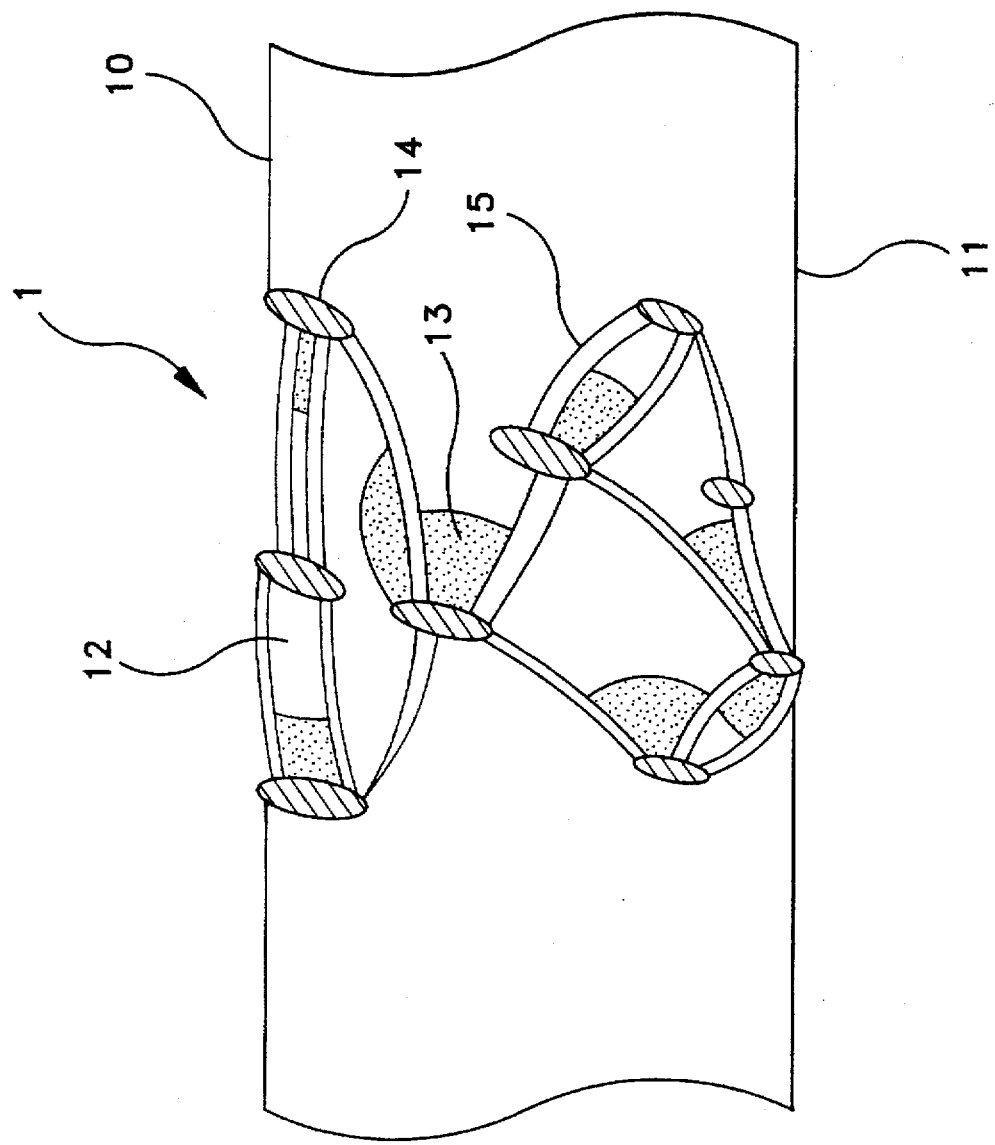
FIG. 1 shows a portion of an implantable expanded PTFE member 1, having walls 10 and 11 nodes 14, fibrils 15, voids 12 and insolubilized biocompatible, biodegradable material 13.
Figure 2:
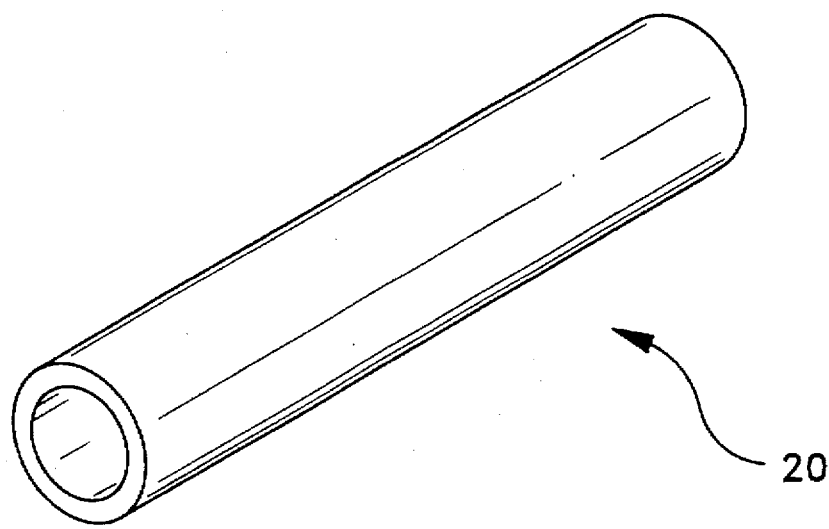
FIG. 2 shows member 1 of FIG. 1 formed into an implantable tubular prosthesis 20.
Figure 3:
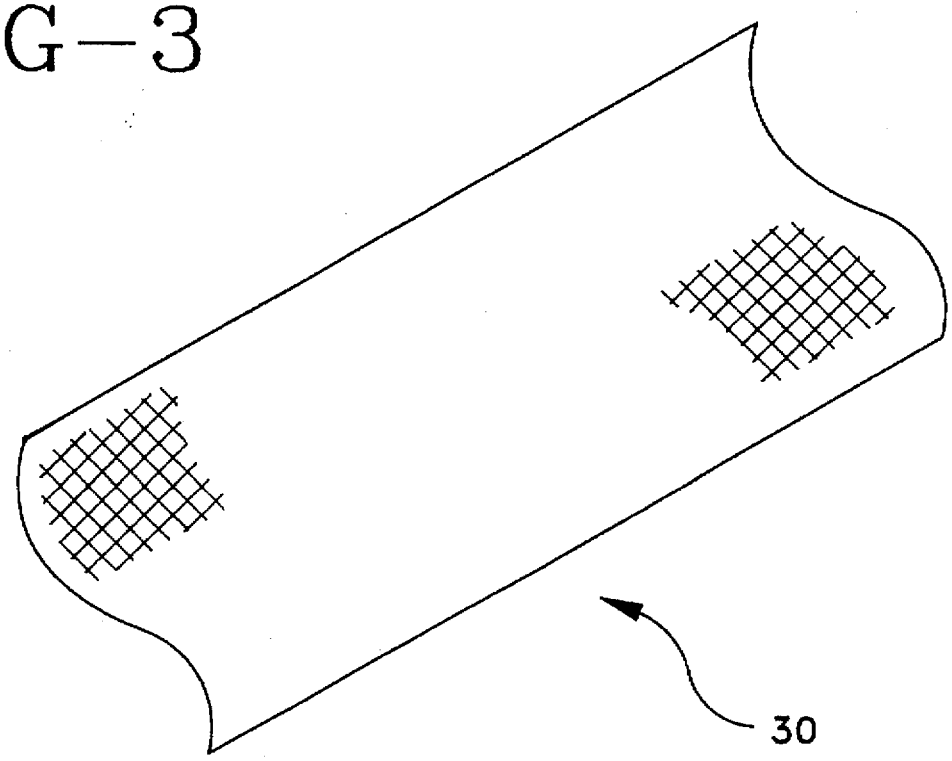
FIG. 3 shows member 1 of FIG. 1 formed into an implantable surgical mesh or patch 30.

For purposes of this invention, the term PTFE shall include fluorinated ethylene propylene polymers and perfluoroalkoxytetrafluoroethylene, as well as polytetrafluoroethylene, all of which are capable of being extruded, stretched and sintered to form porous walled tubular structures e-PTFE). Also for purposes of the present invention, the term tubular protheses shall include vascular prostheses such as grafts, endovascular prostheses and other tubular prostheses useful as implantable devices for the repair, maintenance or replacement of conduit vessels in the body. The preferred prosthetic devices of the present invention are those used in the vascular system. While tubes for vascular use are described as a preferred embodiment of the present invention, it is not limited thereto. Sheets and other structure which may be used or other purposes such as for hernia repair or repair of the myocardium are also within the contemplation of the present invention.

Those biocompatible, biodegradable materials of the present invention are generally extracellular matrix proteins which are known to be involved in cell-to-cell and cell-to-matrix adhesion mechanisms. These materials are selected from the group of extracellular matrix proteins consisting of collagen, including collagen I-V, gelatin, vitronectin, fibronectin, laminin, reconstituted basement membrane matrices such as those marketed under the trademark MATRIGEL® by Collaborative Biomedical Products, Inc. of Bedford, Mass. and derivatives and mixtures thereof. All of these extracellular matrix proteins are capable of being introduced into the voids, preferably via aqueous dispersion or solution and precipitated out to form a solid and optionally undergoing cross-linking to form body fluid insoluble materials. Alternately, the biocompatible, biodegradable material may be introduced in solid form using fluid-pressure or other techniques such as precrosslinking. As used herewith the term biodegradable means it will break down and/or be absorbed in the body. These biocompatible, biodegradable materials preferably substantially fill the voids of the e-PTFE wall and provide a binding substrate of natural origin on which surrounding tissue can easily attach. Rather than merely coat a portion of the e-PTFE, these materials are intended to serve as fillers for the voids.

One of the advantages to using e-PTFE as the material from which tubular prostheses are made is its natural antithrombogenic properties. While the inherent surface chemistry of e-PTFE promotes antithrombogenicity, permanent attachment of the neotima is generally compromised. For example, an outer capsule of perigraft material forms easily around the outer surface of a PTFE prosthesis, but may be easily stripped away. Typically, only a very thin inner capsule is formed on the intraluminal surface of a e-PTFE graft as compared with a conventional textile graft. When this happens, embolization may occur if some or all of the neotima detaches and becomes trapped in small blood vessels. Additionally, suture holes in PTFE prostheses walls generally require compression or topical pressure to accomplish hemostasis.

It is apparent, therefore, that the prostheses of the present invention must reach a balance between the natural antithrombogenic properties of e-PTFE and the properties of collagen which may tend to contribute somewhat to thrombosis formation, while providing a better blood-tight binding surface for tissue ingrowth.

In preparing the prostheses of the present invention, a solution or dispersion of the biocompatible, biodegradable material are separately formed. The extracellular matrix proteins which are used in the dispersions/solutions may be in the soluble form. These materials may be difficult to dissolve in water. Collagen is considered insoluble in water, as is gelatin at ambient temperature. To overcome this difficulty, collagen or gelatin may be preferably formed at acidic pH, i.e. less than 7 and preferably at a pH of about 2 to about 4. The temperature range at which these dispersions/solutions are formed is between about 4° C. to about 40° C., and preferably about 30° C.–35° C.

Type I collagen is the preferred collagen used in the present invention, although other types are contemplated. This molecule is a rod-like structure having an approximate average length of 300 nm and an approximate diameter of about 1.4 nm. These rods, referred to as tropocollagen, are composed of three alpha chains. Each chain is a left-handed helix comprising approximately 1,000 amino acids. The left-handed helix chains are wrapped around one another to form a super right-handed helix.

It is theorized that under physiologic conditions, collagen molecules spontaneously aggregate into units of five molecules which then combine with other 5 unit aggregates in a lateral mode. The larger aggregates then combine with similar aggregates in a linear mode, eventually forming a collagen fiber. Collagen fibers are insoluble in physiologic fluids because of the covalent cross-links that convert collagen into a network of its monomeric elements. Collagen fibers are responsible for the functional integrity of bone, cartilage and skin, as well as reinforcement of the structural framework of the blood vessels and most organs. Collagen is a hydroxy propylene, glycine-type protein which can be denatured by a variety of methods to form gelatin.

Another important property of collagen is that it initiates the clotting response when exposed to whole blood. Thus, collagen present in the voids of the prosthesis contributes to inhibition of prosthesis leakage during and immediately after implantation.

Once the biocompatible, biodegradable material is introduced into the e-PTFE voids and precipitated out into solid form, it is optionally cross-linked. Cross-linking of the material can be accomplished by any conventional method so long as it is not disruptive or have a negative effect on the e-PTFE substrate. For example, in the case of collagen, cross-linking can be accomplished by exposure to an aldehyde vapor then dried to remove excess moisture and an aldehyde or the collagen may be precrosslinked prior to introduction into the voids via a dispersion. In the case of gelatin, cross-linking is effectuated by similar methods.

In one embodiment, the process of preparing the e-PTFE prostheses of the present invention includes using a force to cause the dispersion of biocompatible material to penetrate the tubular walls of the prostheses, thereby contacting the internodal voids. This can be accomplished in a number of ways, such as by clamping one end of the tubular prosthesis, filling the inner lumen with a dispersion of the biocompatible, biodegradable material and using pressure to cause migration of the dispersion into the interstices of the e-PTFE walls. The transluminal flow of the dispersion is believed to permit sufficient contact between the biocompatible, biodegradable materials and the voids. While impregnation time depends on the e-PTFE pore size, graft length, impregnation pressure, collagen concentration and other factors, generally it can be accomplished in a short period of time, for example from less than 1 minute to 10 minutes at a preferred temperature range of 30° C. to 35° C. These parameters are not critical however, provided the voids are substantially filled with the biocompatible, biodegradable material. The soluble biocompatible, biodegradable material may be optionally subjected to cross-linking treatment such that it is solidified in place. For example, cross-linking by exposure to various cross-linking agents and methods such as formaldehyde vapor is then preferably carried out. Subsequent to formation of the cross-linked collagen, the prosthesis can then be rinsed and prepared for sterilization by known methods. Vacuum drying or heat treatment to remove excess moisture and/or cross-linking agents can then be used. The entire process of contacting the e-PTFE with the dispersion/solution can be repeated several times, if necessary, to achieve the desired impregnation.

In a preferred embodiment, the e-PTFE surface of the prosthesis is chemically modified to impart greater hydrophilicity thereto. For example, this can be accomplished by glow discharge plasma treatment or other means whereby hydrophilic moieties are attached to or otherwise associated with the e-PTFE surface. Such treatment enhances the ability of the e-PTFE to imbibe the biocompatible dispersion/solution.

Alternatively, the e-PTFE structure can be rendered hydrophilic by immersion in a solution of water-soluble polymers. Examples of suitable water-soluble polymers include oxygen containing hydrocarbons such as polyvinylalcohol, polyethylene oxide, polyethylene glycol, methyl cellulose, ethyl cellulose, hydroxyethyl cellulose and hydroxypropyl cellulose. Alternatively, the water-soluble polymer can be a nitrogen-containing polymer such as a polyacrylamide, polyvinyl pyrrolidone, polyvinylamine or polyetheleneimine.

Various pharmacological actives such as antimicrobials, antivitals, antibiotics, growth factors, blood clotting modulators such as heparin and the like, as well as mixtures and composite layers thereof can be added to the biocompatible dispersion prior to impregnation into the prosthesis.

In another embodiment of the present invention, the collagen or gelatin dispersion can be insolubilized prior to exposure to the prosthesis. This of course makes impregnation of the prosthesis and filling of the interstitial voids somewhat more difficult.

A preferred method of preparing the prostheses of the present invention includes preparing a mixture, i.e. a solution or dispersion of a known concentration of a biocompatible, biodegradable material selected from the group consisting of collagen, gelatin, derivatives of collagen, derivatives of gelatin and mixtures thereof, having a pH within a range of from about 2 to about 4 and preferably at a pH of about 3.5–3.9. The dispersion should have a low ionic strength, and prepared at temperatures of about 4° C. to about 40° C., and preferably about 30° C. to about 35° C. The e-PTFE surface is preferably modified by enhancing hydrophilicity with glow discharge plasma deposition prior to contacting the prosthesis with the biocompatible dispersion. The tubular prosthesis is then contacted under force with the dispersion to allow for impregnation and transluminary flow of the dispersion through the walls of the prosthesis, thereby substantially filling the interstitial voids. The prostheses are then treated with a chemical solution, such as buffered phosphate at a pH of about 7.4, to insolubilize the biocompatible material in place. Optionally, subsequent formaldehyde vapor exposure can be used to cross-link the material once deposited in the voids. The prosthesis may subsequently be rinsed in a sterilizing solution such as an ethylene oxide solution.

Although illustrative embodiments of the present invention have been described herein, it should be understood that the invention is not limited to those described, and that various other changes or modifications may be made by one skilled in the art without departing from the scope or spirit of the invention.

What is claimed is:

1. A process of preparing an expanded polytetrafluoroethylene (e-PTFE) tubular prosthesis having a microporous wall structure including nodes, internodal spaces and fibrils interconnecting said nodes wherein said internodal spaces have been impregnated with a solid, insoluble biocompatible material, comprising the steps of:

preparing a dispersion or solution of a soluble biocompatible, biodegradable material including extracellular matrix proteins selected from the group consisting of collagen, gelatin, vitronectin, fibronectin, laminin, reconstituted basement membrane matrices and mixtures thereof at an acidic pH;

contacting said prosthesis with said dispersion or solution to impregnate said internodal spaces with said soluble biocompatible material;

increasing the pH of said dispersion or solution to precipitate out said soluble biocompatible, biodegradable material to render it into an insoluble state, whereby said internodal spaces are substantially filled with said insoluble biocompatible, biodegradable material.

2. A process of claim 1 whereby said precipitating out is achieved by treatment with a buffered phosphate solution to form said solid insoluble biocompatible, biodegradable material.

3. A process of claim 2 wherein said solid insoluble biocompatible, biodegradable material is cross-linked by exposure to an aldehyde vapor.

4. A process of claim 1 whereby said e-PTFE structure is rendered hydrophilic by immersion in a solution of water-soluble polymers.

5. The process of claim 4 wherein said water-soluble polymer is an oxygen-containing hydrocarbon selected from the group consisting of polyvinylalcohol, polyethylene oxide, polyethylene glycol, methyl cellulose, ethyl cellulose, hydroxyethyl cellulose and hydroxypropyl cellulose.

6. A process of claim 4 wherein said water-soluble polymer is a nitrogen-containing polymer selected from the group consisting of polyacrylamide, polyvinyl pyrrolidone, polyvinylamine and polyethyleneimine.

7. A processes of claim 1 further comprising a step of rinsing said prosthesis in a sterilizing solution.

8. A process of claim 7 wherein said step of rinsing includes treating with an ethylene oxide solution.

* * * * *